United States Patent [19]
Karlis et al.

[11] Patent Number: 5,476,092
[45] Date of Patent: Dec. 19, 1995

[54] RESUSCITATION MASK WITH NOSE OCCLUDING AND HEAD INCLINING STRUCTURE

[76] Inventors: George Karlis; Andrew Davaris, both of 4 Malvina Street, Burwood, Victoria 3125, Australia

[21] Appl. No.: 122,583

[22] PCT Filed: Apr. 1, 1992

[86] PCT No.: PCT/AU92/00136

§ 371 Date: Jun. 8, 1994

§ 102(e) Date: Jun. 8, 1994

[87] PCT Pub. No.: WO92/17234

PCT Pub. Date: Oct. 15, 1993

[30] Foreign Application Priority Data

Apr. 2, 1991 [AU] Australia ................... PK5352
Nov. 14, 1991 [AU] Australia ................... PK9474

[51] Int. Cl.⁶ ............... A61M 16/00; A62B 18/08; A62B 9/06
[52] U.S. Cl. ............... 128/203.11; 128/206.24; 128/206.29; 128/207.14
[58] Field of Search ........... 128/202.28, 202.29, 128/203.11, 206.24, 206.29, 207.14, 205.25, 205.13

[56] References Cited

U.S. PATENT DOCUMENTS

| 3,252,457 | 5/1966 | Monaco et al. | 128/203.11 |
| 4,449,526 | 5/1984 | Elam . | |
| 4,559,940 | 12/1985 | McGinnis . | |
| 4,579,114 | 4/1986 | Gray et al. . | |
| 4,811,730 | 3/1989 | Milano | 128/202.29 |
| 4,834,085 | 5/1989 | Webster . | |
| 5,005,568 | 4/1991 | Roescher et al. | 128/202.28 |
| 5,121,745 | 6/1992 | Israel | 128/203.11 |

FOREIGN PATENT DOCUMENTS

| 2624025 | 6/1989 | France . | |
| 2459651 | 7/1975 | Germany | 128/202.28 |

*Primary Examiner*—Kimberly L. Asher
*Attorney, Agent, or Firm*—Ladas & Parry

[57] ABSTRACT

A mouth-to-mouth resuscitation device comprising a fluid passage having a donor inlet, a patient outlet and a valve located intermediate said donor inlet and patient outlet, said valve permitting flow of air from said donor inlet to said patient outlet but preventing flow of fluid from said patient outlet to said donor inlet; face sealing means comprising a mask portion through which said fluid passage passes; and nose sealing cushion adapted to seal the nose of said patient when pressed against the underside of the patient's nose.

10 Claims, 1 Drawing Sheet

5,476,092

RESUSCITATION MASK WITH NOSE OCCLUDING AND HEAD INCLINING STRUCTURE

BACKGROUND OF THE INVENTION

The present invention relates to mouth-to-mouth resuscitation devices and more particularly the invention relates to a resuscitation mask which prevents transfer of bodily fluids between the patient and the donor. It will be convenient to describe the invention with reference to use on an unconscious patient who has stopped breathing, however it should be noted that the invention has a wider application.

Mouth-to-mouth resuscitation is an important and valuable respiration technique to ventilate a patient who has stopped breathing or to assist a patient having difficulty breathing. However, particularly in recent times, there are a number of reasons why potential life saving donors may be hesitant to administer mouth-to-mouth resuscitation or may have their own health jeopardized if they do administer mouth-to-mouth resuscitation. First, the prospect of the patient vomiting during the procedure is discouraging. Further the risk of transfer of infection, both from donor to patient but more particularly from patient to donor is a further discouraging factor. The risk of transmission of the AIDS virus, oral herpes, hepatitis B and other serious diseases by exchange of bodily fluids during mouth-to-mouth resuscitation are factors which may influence the decision of a potential donor to refuse to treat a patient and may put the potential donor at risk when he or she has no indication of the health history of the person being resuscitated. This may be more so with emergency workers such as ambulance officers and police who are more frequently exposed to such risks.

Because of the problems outlined above, many devices have been suggested to reduce or eliminate the risk of exchange of bodily fluids during mouth-to-mouth resuscitation and to avoid the risk of transfer of infection.

The resuscitation devices presently available often suffer from one or more problems. First, many of the devices require two hand operation to effectively seal the patient's mouth and nose and hold the device in position. Secondly, many devices do not allow or encourage correct resuscitation technique of reclining the patient's head back such that the patient's airway is properly opened. Further many of the known devices do not actually keep the patient's airway open by keeping the pharynx and larynx open, the patient's teeth apart and mouth open. Many devices also do not allow connection to mechanical air supply devices.

It is an object of the present invention to provide a resuscitation device which overcomes one or more of the above problems.

SUMMARY OF THE INVENTION

According to the present invention there is provided a mouth-to-mouth resuscitation device comprising a fluid passage having a donor inlet, a patient outlet and an intermediate portion, a valve located at said intermediate portion, said valve permitting flow of air from said donor inlet to said patient outlet but preventing flow of fluid from said patient outlet to said donor inlet; and face sealing means comprising a mask portion through which said fluid passage passes; and nose sealing cushion adapted to seal the nose of said patient when pressed against said nostrils.

In a preferred embodiment, the nose sealing cushion has sidewalls and resilient abutment portions defining a recess for positively locating the base of the nose of the patient and adapted to seal the nostrils of said patient when pressed upwardly against the underside of the patient's nose.

The nose sealing cushion is adapted to seal the nose of the patient by occluding the nostrils by pressing underneath the nose in the region of the nasal septum. The cushion means may include resilient abutment portions adapted to press upwards against the nostrils so as to seal the nostrils. Preferably, the cushion means is a soft resilient natural or synthetic rubber material adapted to deform and seal the nostrils when pressed against the nostrils from under the nose. The nose cushion includes a recessed portion into which the base of the nose can be located. The cushion is adapted to seal the nostrils in the area of the nasal septum by positioning the cushion against the nose and applying pressure to the mask upwards relative to the mouth of the patient such that the cushion presses up onto the nose rather than downwards as is the case with conventional masks. The cushion is shaped and has sufficient resilience to occlude the nostrils with preferably only minimal pressure being applied when properly positioned. By pressing the cushion onto the patient's nose upwards relative to the mouth the patient's head will naturally be inclined backwards. This backwards tilting of the head is highly desirable for correct resuscitation procedure as it acts to open the patient's airway by opening the pharynx and larynx.

The fluid passage may comprise a number of components but must allow communication of air from the donor to the patient via the donor inlet and patient outlet. The donor inlet preferably is of a standard size to allow attachment of mechanical respiration means such as "Air-viva" (trade mark) respiration ventilators or other mechanical ventilators to be directly attached to the donor inlet without necessitating removal of the mask from the patient.

The fluid passage preferably has an extended portion which extends from the mask portion into the mouth of the patient terminating in the patient outlet. The extended portion preferably extends into the mouth of the patient and keeps the teeth of the patient apart and hence the mouth open and may direct air onto the soft palate of the mouth of the patient. The extended portion reduces the risk of obstruction of the fluid passage by the tongue of the patient. Preferably extended portion is oval shaped in cross-section.

At the intermediate portion of the fluid passage there is located a valve configured to permit flow of air from the donor inlet to the patient outlet while preventing flow of fluid from the patient outlet to the donor inlet. The valve may be a sliding piston valve. The valve may further include one or more exhaust outlets to permit passage of fluid ie. exhaled air, saliva, blood and/or vomitus from the patient outlet out of the fluid passage by way of the exhaust outlets instead of the donor inlet.

The fluid passage passes through a face sealing means which is necessary to enable air from the donor to be forced into the lungs of the patient. Face sealing means comprises a mask portion which forms a seal in the mouth region of the patient. Preferably the mask portion includes a skirt adapted to press against the face of the patient to seal against the face of the patient. The mask portion may include a resilient cushion adapted to seal against the face of the patient. Preferably, the mask portion is such that minimal pressure need be applied to the device to ensure a proper sealing with the patient's mouth region. Preferably the mask portion is suitably resilient to adapt to a wide range of facial profiles to ensure universal fit on a wide variety of potential patients. Mask portion may include finger grips to facilitate positioning by the donor.

Face sealing means further comprises a nose sealing cushion adapted to seal the nose of the patient by occluding the nostrils of the patient as hereinbefore described.

The invention will now be described in more detail with reference to a preferred embodiment illustrated in the accompanying figures. It is to be understood that the figures and following description relate to a preferred embodiment only and are not intended to limit the scope of the present invention.

DETAILED DESCRIPTION OF THE PREFERRED EMBODIMENT

Figure 1:
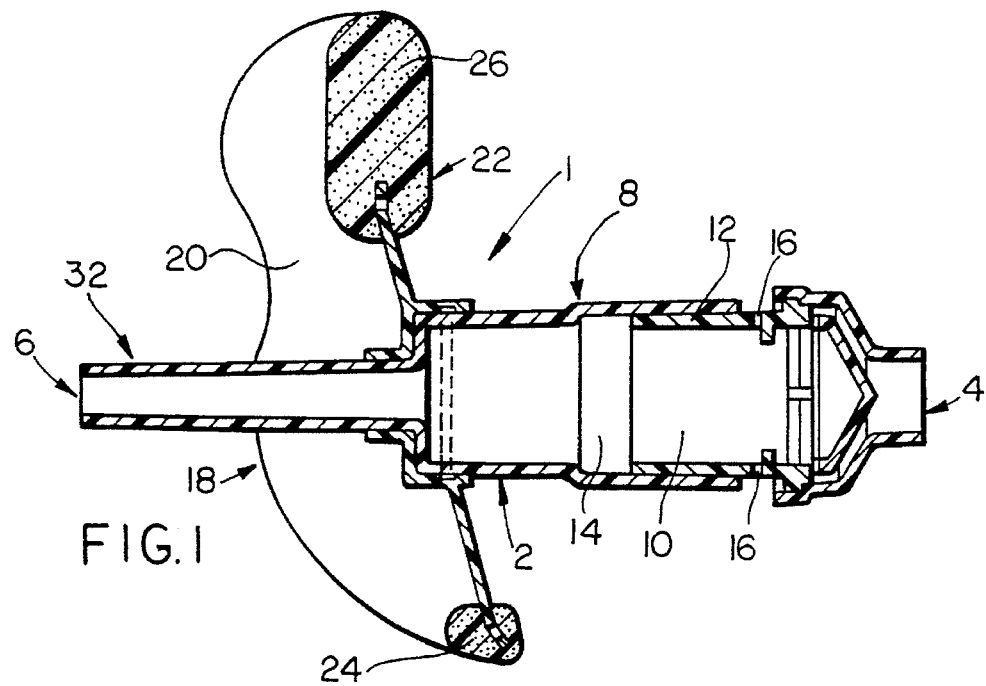
FIG. 1 is a transverse section of a mouth-to-mouth resuscitation device according to the present invention.
Figure 2:
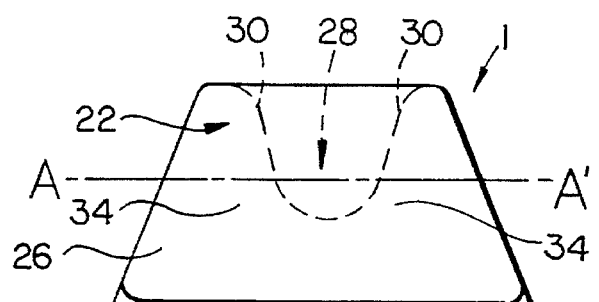
FIG. 2 is an end elevation of a mouth-to-mouth resuscitation device made in accordance with the present invention.
Figure 3:
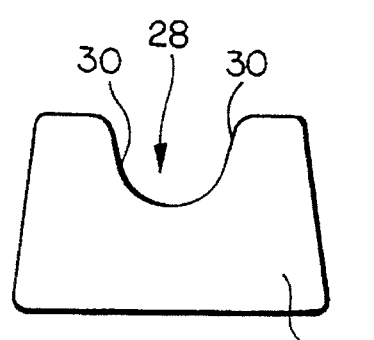
FIG. 3 is a transverse section across line A—A'.

Resuscitation device 1 comprises a fluid passage 2 which has a donor inlet 4 and patient outlet 6. Fluid passage 2 further includes an intermediate portion 8 and a valve 10 located at the intermediate portion 8. The valve 10 permits flow of air from the donor inlet 4 to the patient outlet 6 but prevents flow of fluid from the patient outlet 6 to the donor inlet 4. Valve 10 may comprise a piston element 12 slidably located in a bore 14. Exhaust ports 16 may be provided in the walls of bore 14 at the end of intermediate portion 8 adjacent donor inlet 4.

Resuscitation device 1 further comprises face sealing means 18 consisting of a mask portion 20 and a nose sealing portion 22. Mask portion 20 is adapted to seal the region surrounding the mouth of the patient. Mask portion 20 may include a resilient cushion or skirt means 24 to press against the face of the patient surrounding the patient's mouth. Face sealing means 18 further comprises nose sealing portion 22 consisting of a cushion means 26 adapted to seal the nose of a patient. Cushion means 26 seals the patient's nostrils when pressed upwards relative to the patient's mouth against the nasal septum and blocks the patient's nostrils. Cushion means 26 includes recessed portion 28 into which the patient's nose locates. Resilient abutment portions 32 press against and seal the nostrils of the patient and side walls 30 of recessed portion 28 may press against the nostrils and side of the patient's nose to occlude the nasal airway.

Fluid passage 2 may further include an extended portion 32 which extends into the patient's mouth and terminates at outlet portion 6. Extended portion 32 is adapted to be inserted into the mouth of the patient and to keep the teeth of the patient apart and to keep the mouth of the patient open. Preferably, extended portion 32 is of sufficient length such that patient outlet 6 directs air from the donor onto the soft palate of the patient.

In use, the unconscious patient who is not breathing is put into the usual supine position. Once the patient's mouth has been cleared of foreign matter, ie. vomitus, dentures etc. extended portion 32 is inserted into the mouth of the patient and preferably positioned such that patient outlet 6 is positioned adjacent the soft palate of the patient. Face sealing means 18 is then brought into contact with the patient's face. Mask portion 20 seals the majority of the patient's face around the mouth region by way of cushion 24 which is pressed onto the face of the patient and deforms slightly to form a proper seal. At the same time nose sealing portion 22 is brought into contact with the nose of the patient and pressure is applied to device 1 such that nose sealing portion 22 presses upwardly under the nose of the patient. Recess 28 in conjunction with side walls 30 and resilient cushion 26 occlude the nostrils of the patient and hence block the nasal passages of the patient.

As the mask is of a low profile compared to the patient's face, the donor may place his or her fingers over the mask and grasp the patient's jaw and gently pull the patient's head back at the same time as directing light pressure upwardly towards the patient's nose. In directing light pressure upwardly towards the underside of the patient's nose, the natural tendency is for the patient's head to be forced backwards. This upward pressure facilitates positioning of the patient's head into the preferred position for administering mouth-to-mouth resuscitation as the pharynx of the patient is forced into a position whereby the trachea is opened and the tongue of the patient does not occlude the trachea. As a result of this directed pressure, the donor need only hold resuscitation device 1 with one hand leaving the other hand free. The donor exhales into donor inlet 4 causing valve 10 to open and the exhaled air from the donor passes along fluid passage 2 and out of patient outlet 6 via extended portion 32. Once the donor ceases exhaling the positive pressure in the patient's lungs will cause the patient to exhale at which time valve 10 closes and exhaled air from the patient exits via exhaust ports 16. The donor need not remove his or her mouth from donor inlet 4 when the patient is exhaling. If the patient vomits, vomitus may pass in patient outlet 6 along extended portion 32 and out exhaust ports 16. Exchange of bodily fluids from the patient to the donor is thus prevented.

Furthermore, resuscitation device 1 will usually stay positioned in the patient's mouth if cardiopulmonary resuscitation needs to be applied by the donor. Mechanical resuscitation means such as mechanical ventilator pumps or "Air-Viva" (trade mark) bags may be attached directly onto the donor inlet without removing the device from the patient's face.

The resuscitation device may be made from any suitable material known in the art although preferably such material will be capable of sterilization after use. Preferably the mask portion is a resilient rubber material. Preferably nose sealing cushion and skirt are made from a soft resilient foam such as Kraton (trade mark). Preferably the fluid passage including intermediate portion and valve are made from a polycarbonate although other suitable materials known in the art may be used. The resuscitation device and components may be manufactured using any conventional techniques known in the art.

It is to be understood that various modifications, additions and/or alterations may be made to the parts previously described without departing from the ambit of the present invention.

We claim:

1. A mouth-to-mouth resuscitation device comprising
   a fluid passage having a donor inlet, a patient outlet and a valve located intermediate said donor inlet and patient outlet, said valve permitting flow of air from said donor inlet to said patient outlet but preventing flow of fluid from said patient outlet to said donor inlet;
   face sealing means comprising a mask portion through which said fluid passage passes; and
   a nose sealing cushion comprising means for positively locating the base of a patient's nose, and means for occluding the nostrils of a patient and for receiving an inclining force adapted to incline a patient's head backwards and thereby open the airway, said means for locating the base of a patient's nose comprising sidewalls on said cushion defining a recess therebetween and said means for occluding and force receiving comprising abutment portions of said nose sealing cushion, wherein said nose sealing cushion is used to positively locate the base of the nose of a patient when pressed upwardly against the underside of a patient's nose.

2. A mouth-to-mouth resuscitation device according to claim 1 wherein said nose sealing cushion is a resilient natural or synthetic rubber adapted to deform to seal the nostrils of a patient.

3. A mouth-to-mouth resuscitation device according to claim 1 wherein said fluid passage includes an elongated tube which is adapted to extend into a patient's mouth and terminate at said patient outlet.

4. A mouth-to-mouth resuscitation device according to claim 1 wherein said elongated tube is oval shaped in cross-section.

5. A mouth-to-mouth resuscitation device according to claim 1 wherein said donor inlet is adapted to connect to a mechanical respirator device.

6. A mouth-to-mouth resuscitation device according to claim 1 wherein said valve comprises a piston slidable within said fluid passage and at least one exhaust port in a wall of said fluid passage such that when air is forced into said donor inlet, said valve closes said exhaust port and said air passes out of said patient outlet, whilst when fluid is forced into said patient outlet, said valve opens said exhaust port and said fluid passes out of said exhaust port.

7. A mouth-to-mouth resuscitation device according to claim 1 wherein said mask portion includes hand grip means adapted to receive the fingers of the donor.

8. A mouth-to-mouth resuscitation device according to claim 1 wherein said mask portion includes a resilient skirt adapted to seal against the face of a patient.

9. A method of administering mouth-to-mouth resuscitation to a patient comprising the steps of:

(a) applying to the face of a patient in need resuscitation a mouth-to-mouth resuscitation device comprising a fluid passage having a donor inlet, a patient outlet and a valve located intermediate said donor inlet and patient outlet and at least one exhaust port in said valve permitting flow of air from said donor inlet to said patient outlet but preventing flow of fluid from said patient outlet to said donor inlet;

face sealing means comprising a mask portion through which said fluid passage passes; and nose sealing cushion having sidewalls and resilient abutment portions defining a recess therein and adapted to seal the nostrils of a patent;

(b) pressing said device onto the face of a patient such that said mask portion seals around a patient's mouth, and pressing said device upwards such that said nose sealing cushion abuts and seals the nostrils of a patient and inclining a patient's head backwards to open the airway;

(c) exhaling into said donor inlet to force air out of said patient outlet; and (d) allowing patient exhaled fluid to flow into said donor outlet and out of said fluid passage via said exhaust port.

10. A method according to claim 9 wherein said device further includes an elongated tube terminating in said donor outlet, and said elongated tube is inserted into the mouth of a patient before pressing said device onto the face of a patient.

* * * * *